United States Patent
Chiesi et al.

(10) Patent No.: US 9,645,073 B2
(45) Date of Patent: May 9, 2017

(54) OPTICAL CHAMBER FOR A GAS DETECTION DEVICE

(71) Applicant: Schneider Electric Industries SAS, Rueil Malmaison (FR)

(72) Inventors: Laurent Chiesi, Reaumont (FR); Hynek Raisigel, Sassenage (FR); Gilles Chabanis, Charnecles (FR); Paul Laurens, Pommier de Beaurepaire (FR); Mathias Allely, Gillonnay (FR)

(73) Assignee: SCHNEIDER ELECTRIC INDUSTRIES SAS, Rueil Malmaison (FR)

( * ) Notice: Subject to any disclaimer, the term of this patent is extended or adjusted under 35 U.S.C. 154(b) by 0 days.

(21) Appl. No.: 14/739,103

(22) Filed: Jun. 15, 2015

(65) Prior Publication Data
US 2015/0377767 A1 Dec. 31, 2015

(30) Foreign Application Priority Data

Jun. 26, 2014 (FR) .................................. 14 55984
Jun. 27, 2014 (FR) .................................. 14 56055

(51) Int. Cl.
*G01N 21/03* (2006.01)
*G01N 21/3504* (2014.01)

(52) U.S. Cl.
CPC ....... *G01N 21/0303* (2013.01); *G01N 21/031* (2013.01); *G01N 21/3504* (2013.01); *G01N 2021/0389* (2013.01)

(58) Field of Classification Search
CPC ............. G01N 21/783; G01N 21/3504; G01N 21/031; G01N 21/59; G01N 2021/151; G01N 2021/1704; G01J 3/42

(Continued)

(56) References Cited

U.S. PATENT DOCUMENTS 5,009,493 A * 4/1991 Koch .................... G01N 21/031
356/246
5,065,025 A * 11/1991 Doyle .................... G01N 21/05
250/343

(Continued)

FOREIGN PATENT DOCUMENTS

DE 42 14 840 A1 11/1993
WO WO 98/09152 A1 3/1998
WO WO 02/063283 A1 8/2002

OTHER PUBLICATIONS

French Preliminary Search Report issued Mar. 11, 2015 in French Application 14 56055, filed on Jun. 27, 2014 (with English Translation of Categories of Cited Documents and Written Opinion).

*Primary Examiner* — Hoa Pham
(74) *Attorney, Agent, or Firm* — Oblon, McClelland, Maier & Neustadt, L.L.P.

(57) ABSTRACT

An optical chamber for a gas detection device, which includes reflecting device for reflecting radiation issued from a radiation source and for redirecting the radiation toward a radiation detector, the reflecting device including a first series of adjacent mirrors and a second series of adjacent mirrors. The mirrors of the first series and the mirrors of the second series are of the truncated ellipsoid of revolution type. The first series of mirrors and the second series of mirrors are arranged relative to each other so that the radiation emitted by the radiation source is reflected alternatively by a mirror of the second series and by a mirror of the first series and defines an optical path extending from the radiation source to the radiation detector.

12 Claims, 2 Drawing Sheets

(58) Field of Classification Search
USPC .................................. 356/432–440, 244, 246
See application file for complete search history.

(56) References Cited

U.S. PATENT DOCUMENTS

| | | | |
|---|---|---|---|
| 5,515,859 A * | 5/1996 | Paz | A61B 5/083 |
| | | | 250/339.1 |
| 5,726,752 A * | 3/1998 | Uno | G01N 21/031 |
| | | | 356/244 |
| 6,194,735 B1 | 2/2001 | Martin | |
| 2002/0105650 A1 | 8/2002 | Stuttard | |
| 2005/0017206 A1* | 1/2005 | Tice | G01N 15/06 |
| | | | 250/573 |
| 2006/0227327 A1 | 10/2006 | McNeal et al. | |
| 2008/0212093 A1* | 9/2008 | Moriya | G01N 15/0205 |
| | | | 356/338 |
| 2013/0075615 A1* | 3/2013 | Starta | G01N 21/3504 |
| | | | 250/341.7 |

* cited by examiner

OPTICAL CHAMBER FOR A GAS DETECTION DEVICE

TECHNICAL FIELD OF THE INVENTION

The present invention relates to an optical chamber for gas detection devices and to gas detection devices incorporating such an optical chamber. The invention especially relates to non-dispersive infrared (NDIR) gas detection devices.

PRIOR ART

A gas detection device comprising a radiation source arranged to emit beams of light radiation, a radiation detector and reflecting means forming an optical chamber into which the emitted light radiation is transmitted is known from patent EP 1 987 346 B1. The reflecting means comprise a plurality of adjacent reflective surfaces that are arranged so that each radiation beam emitted by the source is redirected toward the detector directly by one of the reflective surfaces. The reflective surfaces are each defined by an arc of a circle having a radius and a centre.

Another solution is described in patent application EP 2 526 404 A1. In this solution, radiation emitted by the radiation source follows an optical path to the detector through an optical guide. Relative to the preceding patent, this solution has the advantage of lengthening the optical path and therefore of increasing the sensitivity of the device. However, it requires particular attention to be paid to the positioning of the radiation source and detector relative to the optical guide. The slightest movement of the components substantially modifies the signal obtained as output and therefore the precision of the device.

The aim of the invention is to provide an optical chamber for a gas detection device allowing a very satisfactory sensitivity to be obtained for the device without increasing its bulk. The device of the invention including said optical chamber will in particular be insensitive to relative movements of the radiation source and detector with respect to the optical chamber.

SUMMARY OF THE INVENTION

This aim is achieved by way of an optical chamber for a gas detection device, comprising reflecting means for reflecting radiation issued from a radiation source and for redirecting said radiation toward a radiation detector. The reflecting means comprise a first series of adjacent mirrors and a second series of adjacent mirrors. The mirrors of the first series and the mirrors of the second series have two focal points. The first series of mirrors and the second series of mirrors are arranged relative to each other so that the radiation emitted by the radiation source is reflected alternatively by a mirror of the second series and by a mirror of the first series and defines an optical path extending from the radiation source to the radiation detector.

According to the invention, there being n mirrors in the second series and n−1 mirrors in the first series, n being higher than or equal to three, the mirrors are arranged so that:
- a mirror M'i of the second series is arranged to focus the radiation on a mirror Mi of the first series, the mirror Mi being located at the focal point of the mirror M'i of the second series, i being comprised between 1 and n−1;
- a mirror Mi of the first series is arranged to focus the radiation on a mirror M'i+1 of the second series, i being comprised between 1 and n−1;
- a mirror M'i of the second series, where i=n, is arranged to focus the radiation on the detector; and
- a mirror M'i of the second series, where i=1, is arranged to receive the radiation coming from the radiation source.

Advantageously, the mirrors of the first series and the mirrors of the second series are of the truncated ellipsoid of revolution type.

According to another particularity, the mirrors are arranged so that the optical path followed by the radiation follows a circular trajectory.

According to another particularity, the chamber comprises two portions fastened to each other, a lower portion in which the mirrors of the first series are formed and an upper portion joined to the lower portion and in which the mirrors of the second series are formed.

According to another particularity, the mirrors of the first series and the mirrors of the second series have an ellipsoidal shape and each ellipsoidal shape is obtained by moulding in the first portion and second portion of the optical chamber.

According to another particularity, each mirror comprises a reflective surface produced by depositing a reflective layer on the ellipsoidal shape.

According to another particularity, the reflective layer is deposited by PVD or by electrolysis and for example contains gold.

According to another particularity, the optical chamber includes an entrance intended to be located facing the radiation source and an exit to be located facing the radiation detector.

The invention also relates to a detection device comprising a radiation source arranged to emit radiation, a radiation detector and an optical chamber in which the gas to be analysed is located, said chamber being arranged to transmit the radiation from the radiation source to the radiation detector, the optical chamber being such as defined above.

According to one particularity of the device, the radiation source and the radiation detector are arranged side-by-side.

According to another particularity, the radiation source and the radiation detector are fastened to the same electronic board.

According to another particularity, the radiation source comprises at least one light-emitting diode.

According to another particularity, the radiation detector comprises at least one photodiode.

BRIEF DESCRIPTION OF THE FIGURES

Other features and advantages will become apparent from the following detailed description given with regard to the appended drawings, in which.

DETAILED DESCRIPTION OF AT LEAST ONE EMBODIMENT

The invention relates to an optical chamber for a gas detection device and to the corresponding gas detection device. The detection device is intended to determine the concentration of a gas such as carbon dioxide, for example.

Figure 1:
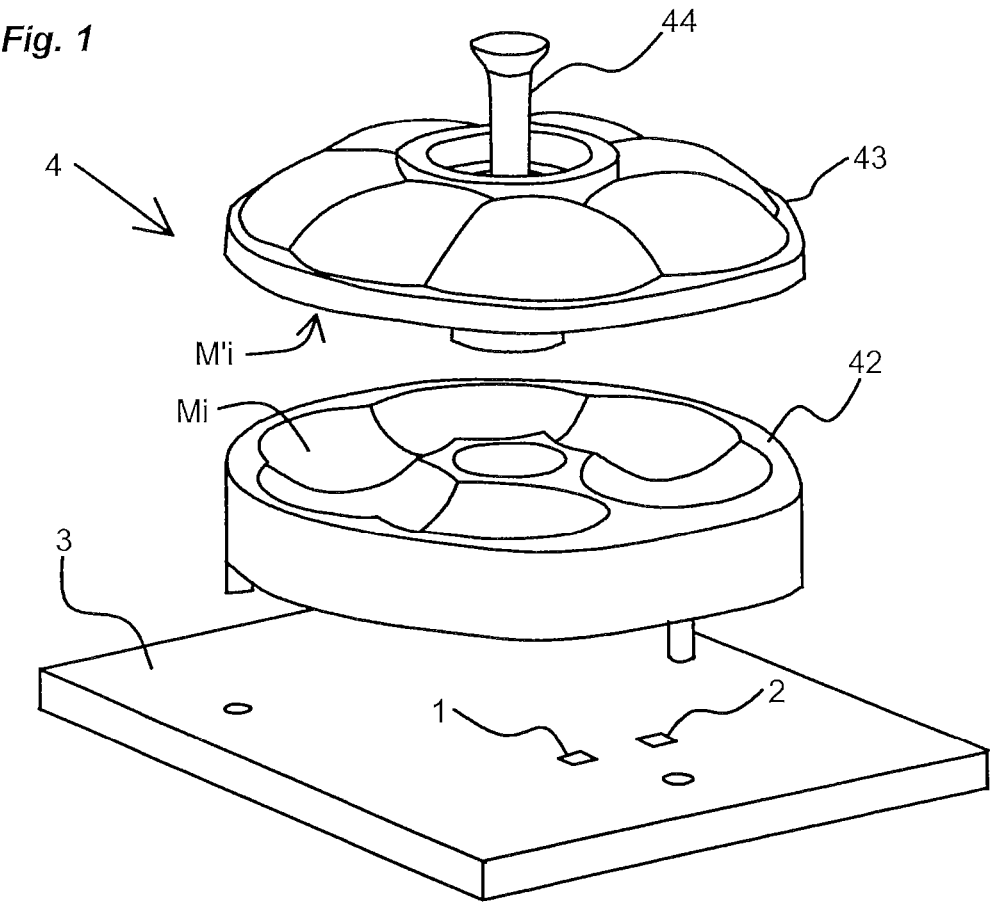
FIG. 1 shows an exploded perspective view of the detection device of the invention.
Figure 3:
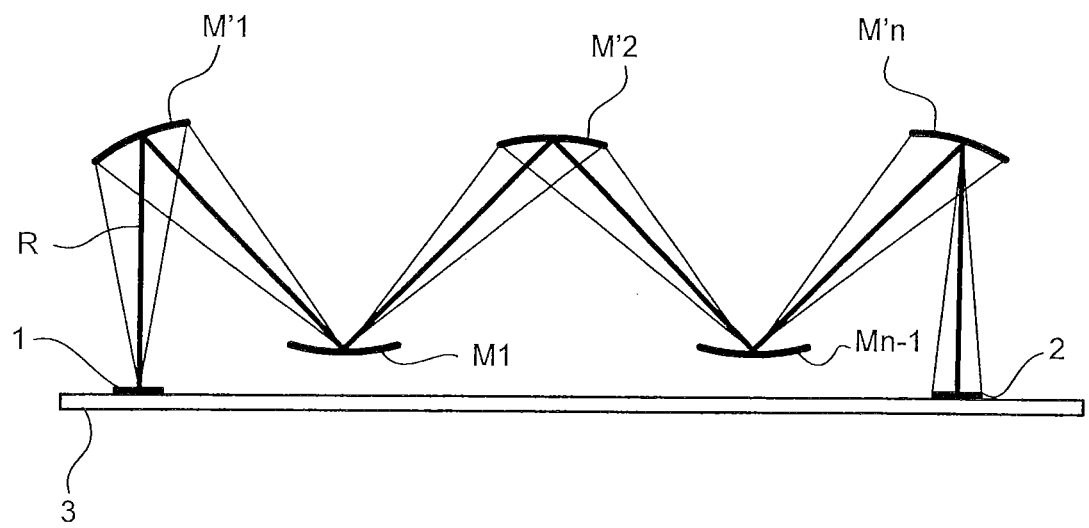
FIG. 3 schematically illustrates the operating principle of the device of the invention.

With reference to FIG. 1, such a device comprises a radiation source 1 for example comprising at least one light-emitting diode arranged to emit radiation (R, FIG. 3).

The device also comprises a radiation detector 2 arranged to detect the radiation emitted by the source 1. The detector 2 for example comprises at least one photodiode intended to sense the radiation emitted by the source 1 and to convert it into an electrical signal to be processed.

Advantageously, the radiation source 1 and the detector 2 are fastened to an electronic board 3 integrated into the device.

Ideally, the radiation source and the detector are positioned on the board side-by-side.

Figure 2:
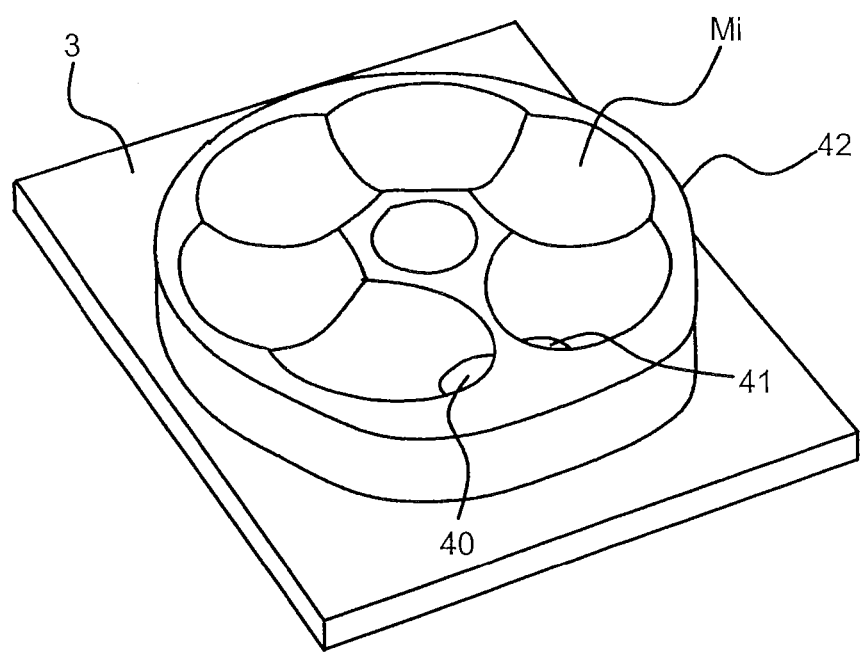
FIG. 2 shows in perspective the bottom portion of the optical chamber of the device.

The device also comprises a closed optical chamber 4, into the interior of which the radiation R is emitted. The optical chamber 4 that is one subject of the invention comprises an entrance 40 in front of which the radiation source 1 is positioned, and an exit 41 in front of which the detector 2 is positioned (FIG. 2).

The optical chamber 4 comprises reflecting means arranged to reflect the radiation R emitted by the source 1 and to make it converge on the detector 2.

According to the invention, the reflecting means comprise a first series of adjacent mirrors Mi and a second series of adjacent mirrors M'i. The first series of mirrors Mi and the second series of mirrors M'i are arranged so that the radiation R emitted by the source 1 is reflected and focused alternatively by a mirror of the second series then by a mirror of the first series so as to follow a zig-zag optical path from the radiation source 1 to the detector 2. To obtain this result, the optical chamber employs mirrors having two focal points. Each mirror thus comprises, following the optical path, a first focal point located upstream of the mirror and a second focal point located downstream of the mirror.

FIG. 3 illustrates this principle:
the radiation source 1 emits radiation that is intended to be received by a first mirror M'1 of the second series, the radiation source 1 being located at the first focal point of the first mirror M'1 of the second series;
the first mirror M'1 of the second series reflects the received radiation R and focuses it on a first mirror M1 of the first series, said mirror M1 being located at the second focal point of the first mirror M'1 of the second series;
the first mirror M1 of the first series reflects the received radiation R and focuses it on a second mirror M'2 of the second series, this second mirror M'2 of the second series being separate from the first mirror M'1 of the second series and located at the second focal point of the first mirror M1 of the first series (the first mirror M'1 of the second series occupying the first focal point of the first mirror M1 of the first series); and
the second mirror M'2 of the second series reflects the received radiation R and focuses it on a second mirror M2 of the first series, this second mirror M2 of the first series being separate from the first mirror M1 of the first series and located at the second focal point of the second mirror M'2 of the second series (the first mirror M1 of the first series occupying the first focal point of the second mirror M'2 of the second series).

The above process continues between mirrors of the first series and mirrors of the second series until the radiation reaches the detector 2. The mirrors are thus arranged to convey the radiation through the interior of the optical chamber of the radiation source 1 as far as the detector 2. Employing mirrors having two focal points means that the radiation is focused from the source to the detector thus allowing a device of high sensitivity to be obtained.

Generally, if there are n mirrors in the second series and n−1 mirrors in the first series, n being higher than or equal to three, it is possible to state that:
a mirror M'i of the second series focuses the radiation R on a mirror Mi of the first series, the mirror Mi being located at the focal point of the mirror M'i of the second series, i being comprised between 1 and n−1;
a mirror Mi of the first series focuses the radiation R on a mirror M'i+1 of the second series, i being comprised between 1 and n−1;
a mirror M'i of the second series, where i=n, focuses the radiation R on the detector; and
a mirror M'i of the second series, where i=1, receives the radiation coming from the radiation source.

Advantageously, the mirrors having two focal points employed in the first series and second series are of the truncated ellipsoid of revolution type. The truncated ellipsoid of revolution shape gives the mirror the property of having two focal points, thereby allowing, by virtue of the arrangement of the invention, a maximum amount of radiation to be focused on the detector 2 and inflections in the interior of the optical chamber 4 to be limited.

Preferably, the first mirror M'1 of the second series is oriented so as to focus the radiation on the first mirror M1 of the first series, is located plumb with the radiation source 1, and has the radiation source 1 located at its first focal point. Preferably, the last mirror M'n is located plumb with the detector 2 and is oriented so as to focus the radiation originating from the mirror Mn−1 of the first series on the detector 2, the detector being located at its second focal point.

Each mirror is for example produced by depositing a reflective layer on a part made of plastic. The reflective layer is for example a gold layer deposited by physical vapour deposition (PVD) or by electrolysis.

Advantageously, the optical chamber 4 is formed from two separate portions 42, 43 that are joined to each other, i.e. an upper portion 43 is fastened to a lower portion 42 so as to obtain a closed optical chamber. A screw 44 is for example provided for fastening the two portions together. The mirrors Mi of the first series are formed in the lower portion 42 and the mirrors M'i of the second series are formed in the upper portion 43. The lower portion 42 comprises a first aperture forming said entrance 40 of the radiation and a second aperture forming said exit 41 of the radiation R. Preferably, the ellipsoidal shape of the mirrors is obtained by moulding in the first portion 42 and in the second portion 43 of the optical chamber. To travel from a mirror of the first series to a mirror of the second series, the radiation produced must each time in the interior of the chamber pass through the plane of the junction between the lower portion and the upper portion of the chamber. The mirrors of the first series and the mirrors of the second series are thus placed in two separate planes parallel to the junction plane defined above.

According to the invention, the mirrors Mi, M'i of the first series and of the second series are arranged so that the radiation follows a circular optical path in the interior of the chamber. This arrangement especially allows the longest possible optical path to be obtained while limiting the bulk of the device.

According to the invention, the optical chamber 4 is fastened directly, via its first portion 42, to the electronic board 3 so that the radiation source 1 and the detector 2 are located facing the entrance 40 of the optical chamber and the exit 41 of the optical chamber, respectively.

The device may comprise integrated processing means (not shown) allowing the electrical signal obtained as output by the detector 2 to be analysed relative to the signal emitted by the source 1, with a view to deducing therefrom the concentration of the gas present in the optical chamber 3. These processing means may also be independent of the device and separate therefrom.

The solution of the invention thus has several advantages that are listed here:
- the device is particularly compact, while allowing an optical path to be provided that is sufficiently long to make the device precise;
- the signal obtained as output is relatively insensitive to relative movements of the source and detector with respect to the entrance and exit of the optical chamber;
- the solution of the invention limits the number of inflections seen by the radiation, these inflections attenuating the optical signal transmitted to the detector; and
- the solution of the invention has a low electrical power consumption especially because a light-emitting diode is used.

The invention claimed is:

1. An optical chamber for a gas detection device, comprising:
   a reflecting device configured to reflect radiation issued from a radiation source and to redirect the radiation toward a radiation detector;
   an entrance located facing the radiation source; and
   an exit located facing the radiation detector,
   wherein:
   the reflecting device includes a first series of adjacent mirrors (Mi), and a second series of adjacent mirrors (M'i);
   the mirrors (Mi) of the first series and the mirrors (M'i) of the second series have two focal points;
   the first series of mirrors and the second series of mirrors are arranged relative to each other so that the radiation emitted by the radiation source is reflected alternatively by a mirror (M'i) of the second series and by a mirror (Mi) of the first series and follows a circular optical path extending from the radiation source to the radiation detector;
   the optical chamber comprises two portions fastened to each other, a lower portion in which the mirrors (Mi) of the first series are formed and an upper portion joined to the lower portion and in which the mirrors (M'i) of the second series are formed;
   each of the first series of mirrors and the second series of mirrors is arranged in an arc in an overhead plan view of the optical chamber;
   a first mirror (Mi) of the first series of adjacent mirrors includes a first opening as the entrance to receive radiation from the radiation source; and
   a last mirror of the first series of adjacent mirrors includes a second opening as the exit to output radiation to the radiation detector.

2. An optical chamber according to claim 1, wherein, there being n mirrors in the second series and n−1 mirrors in the first series, n being greater than or equal to three, the mirrors are arranged so that:
   a mirror M'i of the second series is arranged to focus the radiation on a mirror Mi of the first series, the mirror Mi of the first series being located at the focal point of the mirror M'i of the second series, i being comprised between 1 and n−1;
   a mirror Mi of the first series, said mirror being located at the focal point of the mirror M'i of the second series, is arranged to focus the radiation on a mirror M'i+1 of the second series, i being comprised between 1 and n−1;
   a mirror M'i of the second series, where i=n, is arranged to focus the radiation on the detector; and
   a mirror M'i of the second series, where i=1, is arranged to receive the radiation coming from the radiation source.

3. An optical chamber according to claim 1, wherein the mirrors (Mi) of the first series and the mirrors (M'i) of the second series are of the truncated ellipsoid of revolution type.

4. An optical chamber according to claim 1, wherein the mirrors (Mi) of the first series and the mirrors (M'i) of the second series have an ellipsoidal shape and in that each ellipsoidal shape is obtained by moulding in the lower portion and upper portion of the optical chamber.

5. An optical chamber according to claim 4, wherein each mirror comprises a reflective surface produced by depositing a reflective layer on the ellipsoidal shape.

6. An optical chamber according to claim 5, wherein the reflective layer is deposited by PVD or by electrolysis.

7. An optical chamber according to claim 5, wherein the reflective layer contains gold.

8. A detection device comprising:
   a radiation source configured to emit radiation;
   a radiation detector; and
   an optical chamber in which gas to be analyzed is located, said optical chamber being configured to transmit the radiation emitted from the radiation source to the radiation detector,
   wherein the optical chamber includes:
   a reflecting device configured to reflect radiation issued from the radiation source and to redirect the radiation toward the radiation detector;
   an entrance located facing the radiation source; and
   an exit located facing the radiation detector; and
   wherein:
   the reflecting device has a first series of adjacent mirrors (Mi), and a second series of adjacent mirrors (M'i);
   the mirrors (Mi) of the first series and the mirrors (M'i) of the second series have two focal points;
   the first series of mirrors and the second series of mirrors are arranged relative to each other so that the radiation emitted by the radiation source is reflected alternatively by a mirror (M'i) of the second series and by a mirror (Mi) of the first series and follows a circular optical path extending from the radiation source to the radiation detector;
   the optical chamber comprises two portions fastened to each other, a lower portion in which the mirrors (Mi) of the first series are formed and an upper portion joined to the lower portion and in which the mirrors (M'i) of the second series are formed;
   each of the first series of mirrors and the second series of mirrors is arranged in an arc in an overhead plan view of the optical chamber;
   a first mirror (Mi) of the first series of adjacent mirrors includes a first opening as the entrance to receive radiation from the radiation source; and
   a last mirror of the first series of adjacent mirrors includes a second opening as the exit to output radiation to the radiation detector.

9. The device according to claim 8, wherein the radiation source and the radiation detector are arranged side-by-side.

10. The device according to claim 9, wherein the radiation source and the radiation detector are fastened to a same electronic board.

11. The device according to claim 8, wherein the radiation source includes at least one light-emitting diode.

12. The device according to claim 8, wherein the radiation detector includes at least one photodiode.

\* \* \* \* \*